United States Patent
Morgan et al.

(10) Patent No.: US 11,020,097 B2
(45) Date of Patent: Jun. 1, 2021

(54) ASSISTIVE DEVICE FOR REMOVING A BIOLOGICAL SAMPLE FROM AN INTRAOSSEOUS DEVICE, AND RELATED KITS AND METHODS

(71) Applicant: Teleflex Life Sciences Limited, Valletta (MT)

(72) Inventors: John Morgan, Shavano Park, TX (US); Larry J. Miller, Shavano Park, TX (US); Robert W. Titkemeyer, Shavano Park, TX (US); Chris Kilcoin, Shavano Park, TX (US)

(73) Assignee: TELEFLEX LIFE SCIENCES LIMITED, Valletta (MT)

( * ) Notice: Subject to any disclaimer, the term of this patent is extended or adjusted under 35 U.S.C. 154(b) by 263 days.

(21) Appl. No.: 14/616,330

(22) Filed: Feb. 6, 2015

(65) Prior Publication Data
US 2015/0223786 A1 Aug. 13, 2015

Related U.S. Application Data

(60) Provisional application No. 61/937,365, filed on Feb. 7, 2014.

(51) Int. Cl.
*A61B 10/02* (2006.01)
*A61B 10/00* (2006.01)

(52) U.S. Cl.
CPC ...... *A61B 10/025* (2013.01); *A61B 2010/009* (2013.01); *A61B 2010/0258* (2013.01)

(58) Field of Classification Search
None
See application file for complete search history.

(56) References Cited

U.S. PATENT DOCUMENTS 4,256,119 A * 3/1981 Gauthier ............ A61B 10/0283
600/567
4,630,616 A * 12/1986 Tretinyak ............ A61B 10/025
600/566

(Continued)

FOREIGN PATENT DOCUMENTS

CN 1895182 A 1/2007
CN 101365390 A 2/2009

(Continued)

OTHER PUBLICATIONS

"Fixed." Merriam-Webster.com Dictionary, Merriam-Webster, https://www.merriam-webster.com/dictionary/fixed. Accessed Jun. 12, 2020. (Year: 2020).*

(Continued)

*Primary Examiner* — Matthew Kremer
(74) *Attorney, Agent, or Firm* — BakerHostetler

(57) ABSTRACT

Assistive apparatuses or devices, kits, and methods for assisting with removal of a biological sample from an intraosseous device are described. Some of the present assistive apparatuses comprise: a body including a first end and a second end, and defining a channel with a first portion having a first transverse dimension, a second portion disposed between the first portion and the second end and having a second transverse dimension that is smaller than the first transvers dimension, and a longitudinal axis extending through the first portion and the second portion, the body further including a protrusion extending laterally outward relative to the longitudinal axis; where the channel is configured to receive a portion of an intraosseous device having a hub and a cannula extending from the hub, with the first portion of the channel receiving a part of the hub, and the second portion of the channel receiving a part of the cannula (Continued)

while preventing passage of the hub through the second portion.

18 Claims, 13 Drawing Sheets

(56) References Cited

U.S. PATENT DOCUMENTS

| | | | |
|---|---|---|---|
| 5,843,001 A | | 12/1998 | Goldenberg |
| 7,850,620 B2 | | 12/2010 | Miller et al. |
| 8,641,715 B2 | | 2/2014 | Miller |
| 9,161,775 B1 | * | 10/2015 | Katra ................ A61B 17/3209 |
| 9,750,508 B1 | * | 9/2017 | Barnes ............... A61B 17/1671 |
| 2004/0127814 A1 | | 7/2004 | Negroni |
| 2007/0100201 A1 | * | 5/2007 | Komiya ............. A61B 1/00133 |
| | | | 600/106 |
| 2008/0262383 A1 | * | 10/2008 | Routhier ............. A61B 10/025 |
| | | | 600/567 |
| 2010/0204611 A1 | * | 8/2010 | Zambelli ............ A61B 10/025 |
| | | | 600/567 |
| 2010/0292532 A1 | * | 11/2010 | Kadykowski .......... A61B 17/32 |
| | | | 600/104 |
| 2011/0082387 A1 | | 4/2011 | Miller et al. |
| 2011/0251518 A1 | | 10/2011 | Swisher et al. |
| 2012/0265097 A1 | * | 10/2012 | Melchiorri ......... A61B 10/0266 |
| | | | 600/567 |

FOREIGN PATENT DOCUMENTS

| | | |
|---|---|---|
| CN | 201394032 Y | 2/2010 |
| CN | 103284762 A | 9/2013 |
| GB | 2 347 862 A | 9/2000 |
| WO | 2008033874 A2 | 3/2008 |

OTHER PUBLICATIONS

European Search Report issued in European Patent Application No. 15746455.3 dated Jul. 31, 2017.
International Search Report (ISR) dated May 14, 2015 for PCT/US2015/014806.

* cited by examiner

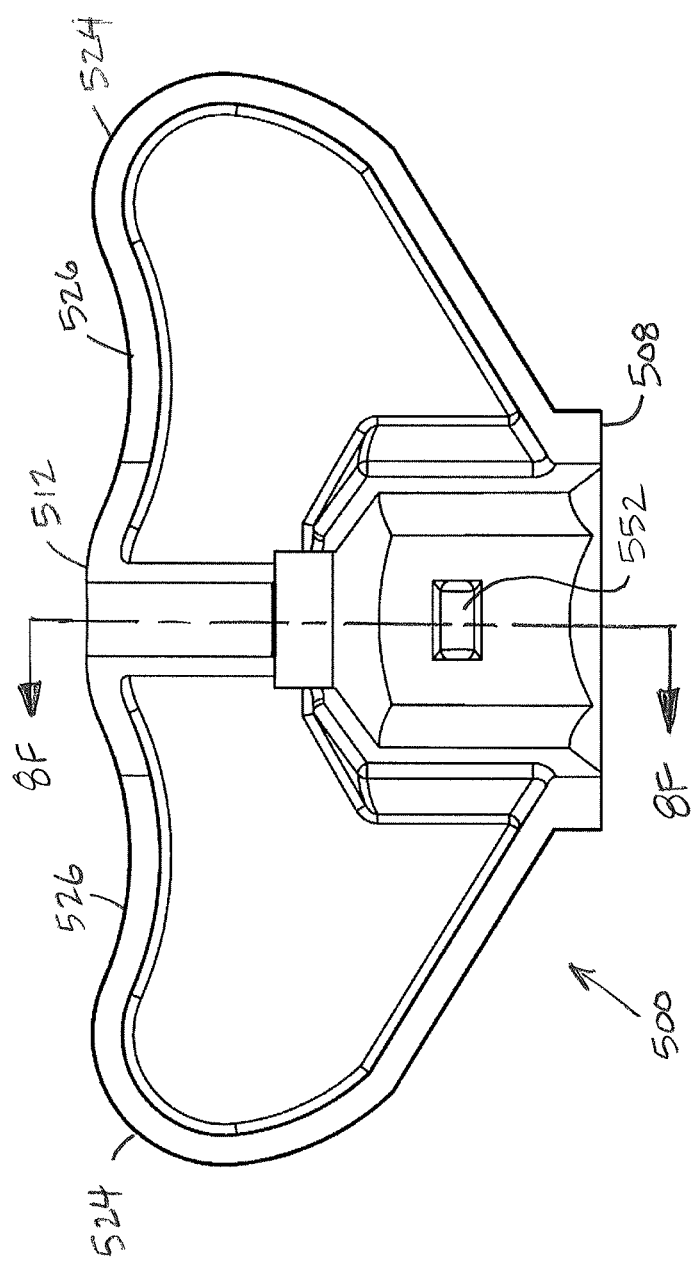
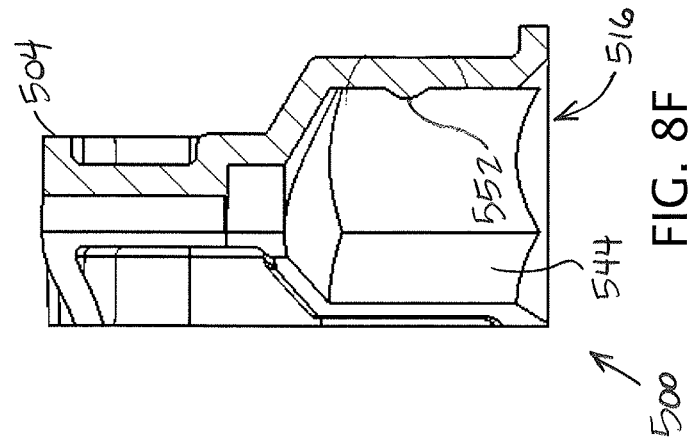

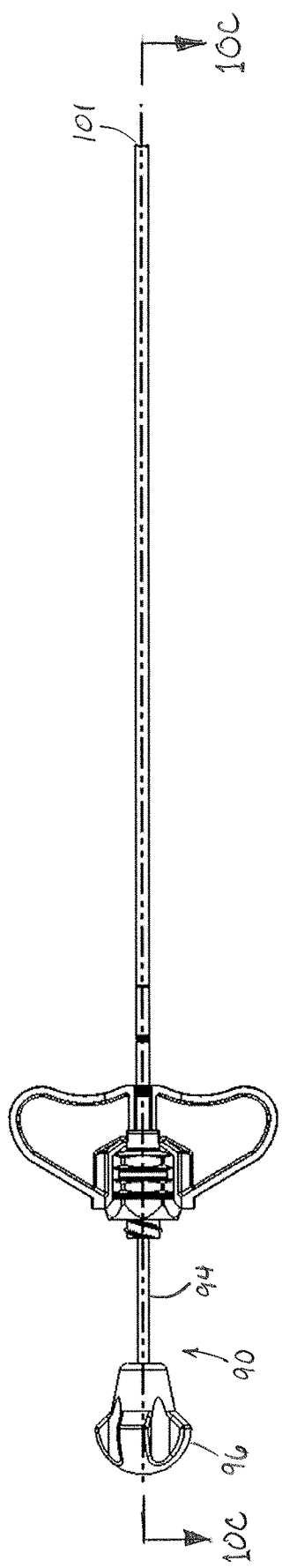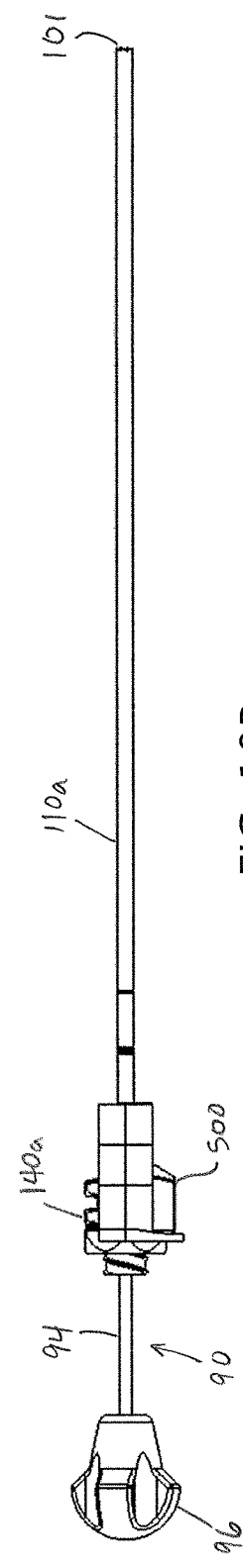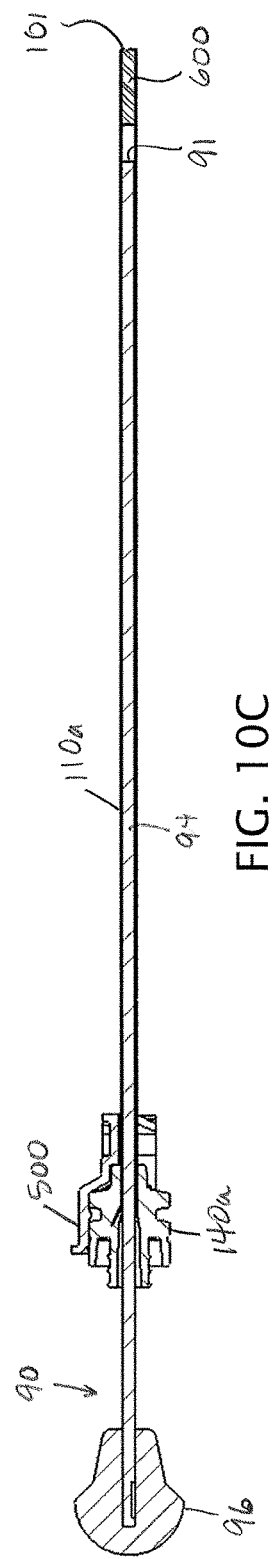
FIG. 10A
FIG. 10B
FIG. 10C

ASSISTIVE DEVICE FOR REMOVING A BIOLOGICAL SAMPLE FROM AN INTRAOSSEOUS DEVICE, AND RELATED KITS AND METHODS

CROSS-REFERENCE TO RELATED APPLICATION

This application claims benefit to U.S. Provisional Patent Application No. 61/937,365 filed Feb. 7, 2014, which is incorporated by reference in its entirety.

FIELD OF INVENTION

The present invention is generally related to extraction of a biological sample from a needle and more particularly, but not by way of limitation, to assistive devices for removing a biological sample from an intraosseous needle.

BACKGROUND

Examples of ejectors and assistive devices are disclosed in U.S. Pat. No. 7,850,620.

SUMMARY

Embodiments of the present methods and systems can be configured to assist a user with removing a biological sample from an intraosseous (JO) device, such as, for example, a hollow penetrator for extracting a bone marrow sample from a patient's bone.

Some embodiments of the present kits comprise: an intraosseous device (comprising: a hub having a first end, a second end, and an opening extending from the first end to the second end; and a cannula extending from the second end of the hub to a distal end spaced from the hub by a first length, the cannula defining a lumen in fluid communication with the opening of the hub); an ejector (comprising: a head; and an elongated member extending from the head to a distal end spaced from the head by a second length at least as large as the first length, the elongated member configured to be inserted into the lumen of the cannula); and an assistive device comprising a body defining a channel having a longitudinal axis and configured to removably receive a portion of the cannula and prevent passage of the hub through the channel, the body further including at least one protrusion extending laterally outward relative to the longitudinal axis of the channel; where the assistive device is configured to receive the at least a portion of the cannula in the channel of the assistive device such that, if the elongated member is inserted into the lumen of the cannula through the opening in the hub, the head and assistive device can be pushed together to cause the distal end of the elongated member to push a biological sample through the distal end of the cannula.

In some embodiments of the present kits, the body of the assistive device includes a first end and a second end, and defines a channel with a first portion having a first transverse dimension, a second portion disposed between the first portion and the second end and having a second transverse dimension that is smaller than the first transvers dimension, the longitudinal axis extends through the first portion and the second portion, and the channel is configured to receive a portion of the intraosseous device with the first portion of the channel receiving a part of the hub, and the second portion of the channel receiving a part of the cannula while preventing passage of the hub through the second portion. In some embodiments, the body of the assistive device further includes a second protrusion extending outwardly relative to the longitudinal axis. In some embodiments, the second protrusion is substantially opposite the first protrusion. In some embodiments, each protrusion of the assistive device defines a gripping surface facing away from the first end of the body of the assistive device. In some embodiments, the hub of the intraosseous device has a non-circular perimeter and the first portion of the channel in the assistive device is shaped to prevent rotation of the hub relative to the assistive device when the portion of the intraosseous device is disposed in the channel. In some embodiments, the first portion of the channel is defined by a plurality of planar surfaces. In some embodiments of the present kits, the planar surfaces are configured to prevent rotation of the hub relative the assistive device when the hub is disposed in the channel of the assistive device. In some embodiments, the hub of the intraosseous device has an equilateral polygonal cross-sectional shape, and the first portion of the channel in the assistive device has a corresponding cross-sectional shape. In some embodiments, the hub includes a recess and the body of the assistive devices includes a protrusion extending into the second portion of the channel in the assistive device that is configured to extend into the recess to resist movement of the hub away from the second portion of the channel when the portion of the intraosseous device is disposed in the channel of the assistive device. In some embodiments, the recess extends around the longitudinal axis. In some embodiments, a lateral portion of the channel in the body of the assistive device is open between the first end and the second end of the body.

Some embodiments of the present apparatuses (e.g., for assisting with removal of a biological sample from an intraosseous device) comprise: a body including a first end and a second end, and defining a channel with a first portion having a first transverse dimension, a second portion disposed between the first portion and the second end and having a second transverse dimension that is smaller than the first transvers dimension, and a longitudinal axis extending through the first portion and the second portion, the body further including a protrusion extending laterally outward relative to the longitudinal axis; where the channel is configured to receive a portion of an intraosseous device having a hub and a cannula extending from the hub, with the first portion of the channel receiving a part of the hub, and the second portion of the channel receiving a part of the cannula while preventing passage of the hub through the second portion.

In some embodiments of the present apparatuses, the body further includes a second protrusion extending outwardly relative to the longitudinal axis. In some embodiments, the second protrusion is substantially opposite the first protrusion. In some embodiments, each protrusion defines a gripping surface facing away from the first end of the body. In some embodiments, the first portion of the channel in the assistive device has a non-circular cross-sectional shape configured to prevent rotation of a hub of an intraosseous device relative to the body when the portion of the intraosseous device is disposed in the channel. In some embodiments, the first portion of the channel is defined by a plurality of planar surfaces. In some embodiments, the planar surface are configured to prevent rotation of a hub of an intraosseous device relative to the body when the hub is disposed in the channel. In some embodiments, the first portion of the channel in the body has an equilateral polygonal cross-sectional shape. In some embodiments, the body includes a protrusion extending into the second portion of the channel configured to extend into a recess in a hub of an intraosseous device that is disposed in the channel to resist movement of the intraosseous device away from the second portion of the channel. In some embodiments, a lateral portion of the channel in the body of the assistive device is open between the first end and the second end of the body.

Some embodiments of the present methods comprise: disposing a portion of an intraosseous device in a channel of an assistive device, the intraosseous device comprising a hub having an opening and a cannula extending from the hub to a distal end, the assistive device comprising a body defining a channel having a longitudinal axis and receiving a portion of the cannula and preventing passage of the hub through the channel, the body further including at least one protrusion extending laterally outward relative to the longitudinal axis of the channel; inserting an elongated member of an ejector into a lumen of the cannula through the opening in the hub, the ejector further comprising a head at one end of the elongated member; and pushing the head and assistive device together to cause a distal end of the elongated member to push a biological sample through the distal end of the cannula.

In some embodiments of the present methods, the body of the assistive device includes a first end and a second end, and defines a channel with a first portion having a first transverse dimension, a second portion disposed between the first portion and the second end and having a second transverse dimension that is smaller than the first transvers dimension, the longitudinal axis extends through the first portion and the second portion, and the channel receives a portion of the intraosseous device with the first portion receiving a part of the hub, and the second portion receiving a part of the cannula while preventing passage of the hub through the second portion. In some embodiments, the body of the assistive device further includes a second protrusion extending outwardly relative to the longitudinal axis. In some embodiments, the second protrusion is substantially opposite the first protrusion. In some embodiments, each protrusion of the assistive device defines a gripping surface facing away from the first end of the body of the assistive device. In some embodiments, the hub of the intraosseous device has a non-circular perimeter and the first portion of the channel in the assistive device is shaped to prevent rotation of the hub relative to the assistive device. In some embodiments, the first portion of the channel is defined by a plurality of planar surfaces. In some embodiments, the planar surfaces are configured to prevent rotation of the hub relative the assistive device. In some embodiments, the hub of the intraosseous device has an equilateral polygonal cross-sectional shape, and the first portion of the channel in the assistive device has a corresponding cross-sectional shape. In some embodiments, the hub includes a recess and the body of the assistive devices includes a protrusion extending into the second portion of the channel in the assistive device that is configured to extend into the recess to resist movement of the hub away from the second portion of the channel. In some embodiments, the recess extends around the longitudinal axis. In some embodiments, a lateral portion of the channel in the body of the assistive device is open between the first end and the second end of the body.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, an apparatus that "comprises," "has," "includes," or "contains" one or more elements possesses those one or more elements, but is not limited to possessing only those elements. Likewise, a method that "comprises," "has," "includes," or "contains" one or more steps possesses those one or more steps, but is not limited to possessing only those one or more steps.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The embodiments of the present assistive devices, coupler assemblies, drivers, intraosseous (IO) devices, and their components shown in the figures are drawn to scale for at least the embodiments shown.

FIGS. 8C-8E depict various orthogonal views of the assistive device of FIGS. 8A-8B.

FIG. 8F depicts a side cross-sectional view of the assistive device of FIGS. 8A-8B, taken along the line 8F-8F of FIG. 8E.

FIGS. 10A-10B depict additional side views illustrating the assembly of the assistive device of FIGS. 8A-8B with an intraosseous device and the ejector of FIG. 7.

FIG. 10C depicts a side cross-sectional view, taken along the line 10C-10C of FIG. 10A, illustrating assembly of the assistive device of FIGS. 8A-8B with an intraosseous device and the ejector of FIG. 7.

DETAILED DESCRIPTION OF ILLUSTRATIVE EMBODIMENTS

Figure 1A:
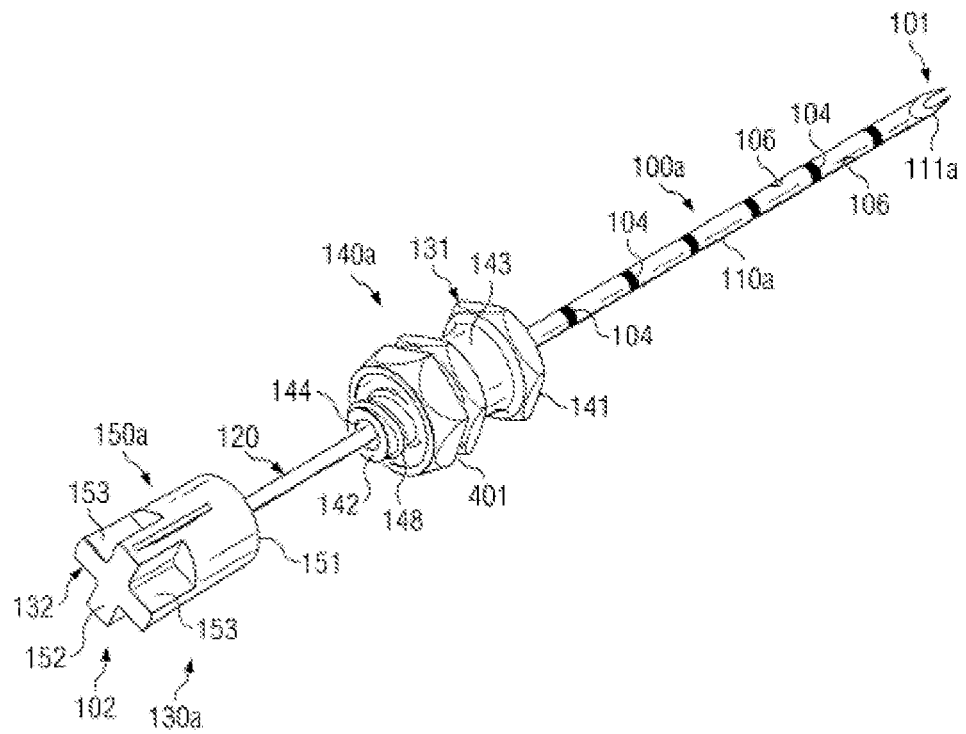
FIG. 1A depicts a perspective view of one embodiment of the present intraosseous devices having a first embodiment of a cannula and a first embodiment of a stylet.

Embodiments of the present powered drivers may be used to insert an IO device incorporating teachings of the present disclosure into a selected target area or target site in ten seconds or less. However, various teachings of the present disclosure are not limited to use with powered drivers. Manual drivers and spring powered drivers may also be used with IO devices incorporating teachings of the present disclosure. Examples of manual drivers are shown in U.S. Pat. No. 8,641,715.

The term "fluid" may be used in this application to include liquids such as, but not limited to, blood, water, saline solutions, IV solutions, plasma, or any mixture of liquids, particulate matter, dissolved medication, and/or drugs associated with biopsy or aspiration of bone marrow or communication of fluids with bone marrow or other target sites. The term "fluid" may also be used in this patent application to include any body fluids and/or liquids containing particulate matter such as bone marrow and/or cells which may be withdrawn from a target area.

The terms "harvest" and "harvesting" may be used in this application to include bone and/or bone marrow biopsy and bone marrow aspiration. Bone and/or bone marrow biopsy (sometimes referred to as "needle biopsy") may be generally described as removing a relatively small piece or specimen of bone and/or bone marrow from a selected target area for biopsy purposes. Bone marrow aspiration (sometimes referred to as "bone marrow sampling") may be generally described as removing larger quantities of bone marrow from a selected target area. Relatively large quantities of bone marrow may be used for diagnostic, transplantation, and/or research purposes. For example some stem cell research techniques may require relatively large quantities of bone marrow.

The term "insertion site" may be used in this application to describe a location on a bone at which an intraosseous device may be inserted or drilled into the bone and associated bone marrow. Insertion sites are generally covered by skin and soft tissue. The term "target area" refers to any location on or within biological material, such as the biological material of a living human being.

The term "intraosseous (IO) device" may be used in this application to include, but is not limited to, any hollow needle, hollow drill bit, penetrator assembly, bone penetrator, catheter, cannula, trocar, stylet, inner penetrator, outer penetrator, IO needle, biopsy needle, aspiration needle, IO needle set, biopsy needle set or aspiration needle set operable to access or provide access to an intraosseous space or interior portions of a bone. Such IO devices may be formed, at least in part, from metal alloys such as 304 stainless steel and other biocompatible materials associated with needles and similar medical devices.

Embodiments of the present drivers and drive systems can be included in medical procedure trays such as those disclosed in U.S. Pat. No. 7,850,620.

The devices and components shown in FIGS. 1A to 7 are prior art devices and components, and the following description of them is provided to give the reader context for the types of devices and components that can be used consistently with embodiments of the present drivers, drive systems, and kits.

Referring now to the drawings, and more particularly to FIG. 1A, shown therein and designated by the reference numeral 100a is one embodiment of the present intraosseous (IO) needle sets or aspiration needle sets. Aspiration needle set 100a comprises a hollow outer penetrator or cannula 110a, a corresponding inner penetrator or stylet (or trocar) 120, and a hub assembly 130a. In the embodiment shown, first end 111a of cannula 110a and first end 121 of stylet 120 are operable or configured to penetrate a bone and associated bone marrow. Various features of first end 111a of cannula 110a and first end 121 of stylet 120 are shown in more detail in FIGS. 1B-1D. First end 101 of IO needle set 100a corresponds generally with first end 111a of cannula 110a and first end 121 of stylet 120.

In the embodiment shown, cannula 110a includes a plurality of markings 104 disposed on exterior portions of the cannula. Markings 104 may be referred to as "positioning marks" or "depth indicators," and may be used to indicate the depth of penetration of needle set 100a into a bone and associated bone marrow. In some embodiments, cannula 110a may have a length of approximately sixty (60) millimeters and/or a nominal outside diameter of approximately 0.017 inches (e.g., corresponding generally to the dimensions of a sixteen (16) gauge needle). Cannula 110a and/or stylet 120 may be formed from stainless steel or other suitable biocompatible materials. In some embodiments, markings 104 are spaced at one (1) centimeter intervals on exterior portions of cannula 110a. In some embodiments, one or more side ports 106 may be formed in exterior portions of cannula 110a spaced from first end 111a.

Hub assembly 130a may be configured and/or used to releasably dispose stylet 120 within the longitudinal bore or lumen of cannula 110a. In the embodiment shown, hub assembly 130a includes a first hub 140a and a second hub 150a. A second end of cannula 110a, opposite from first end 111a, may be securely engaged with hub 140a. The second end of stylet 120, opposite from first end 121, may be securely engaged with the first end of hub 150a. As shown in FIG. 1A, cannula 110a may extend longitudinally from first end 141 of hub 140a. Stylet 120 may also extend from the first end of hub 150*a*. The second end of hub 140*a* may include a standard Luer lock fitting which may be releasably engaged with a corresponding Luer lock fitting disposed within the first end of second hub 150*a*. The Luer lock fitting disposed on the second end of hub 140*a* may be in fluid communication with the bore or passage in cannula 110*a*, and may be operable to be releasably engaged with a standard syringe type fitting and/or a standard intravenous (IV) connection. In the embodiment shown, hub 150*a* includes second end 152 that generally corresponds with second end 132 of hub assembly 130*a* and second end 102 of IO needle set 100*a*. Hub 140*a* may include first end 141 which may generally correspond with first end 131 of hub assembly 130*a*. Cannula 110*a* may extend longitudinally from first end 141 of hub 140*a* and first end 131 of hub assembly 130.

Figure 6C:
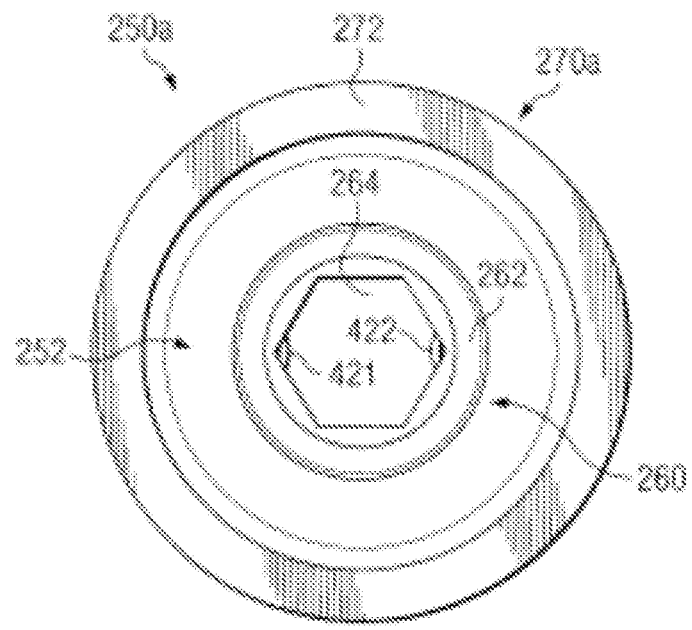
FIGS. 6A-6C depict various views of the coupler assembly of FIG. 3.
Figure 6A:
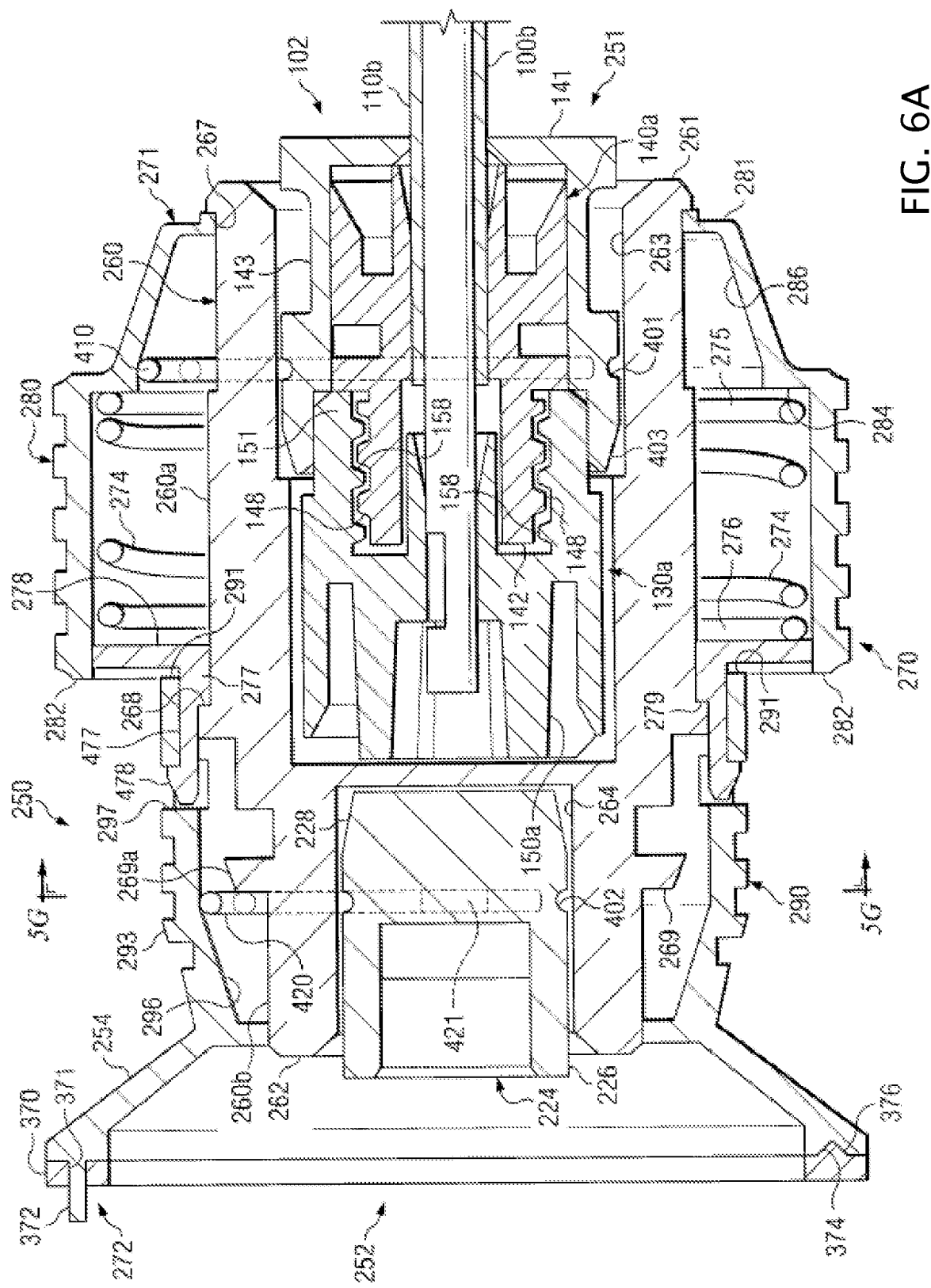
Figure 6B:
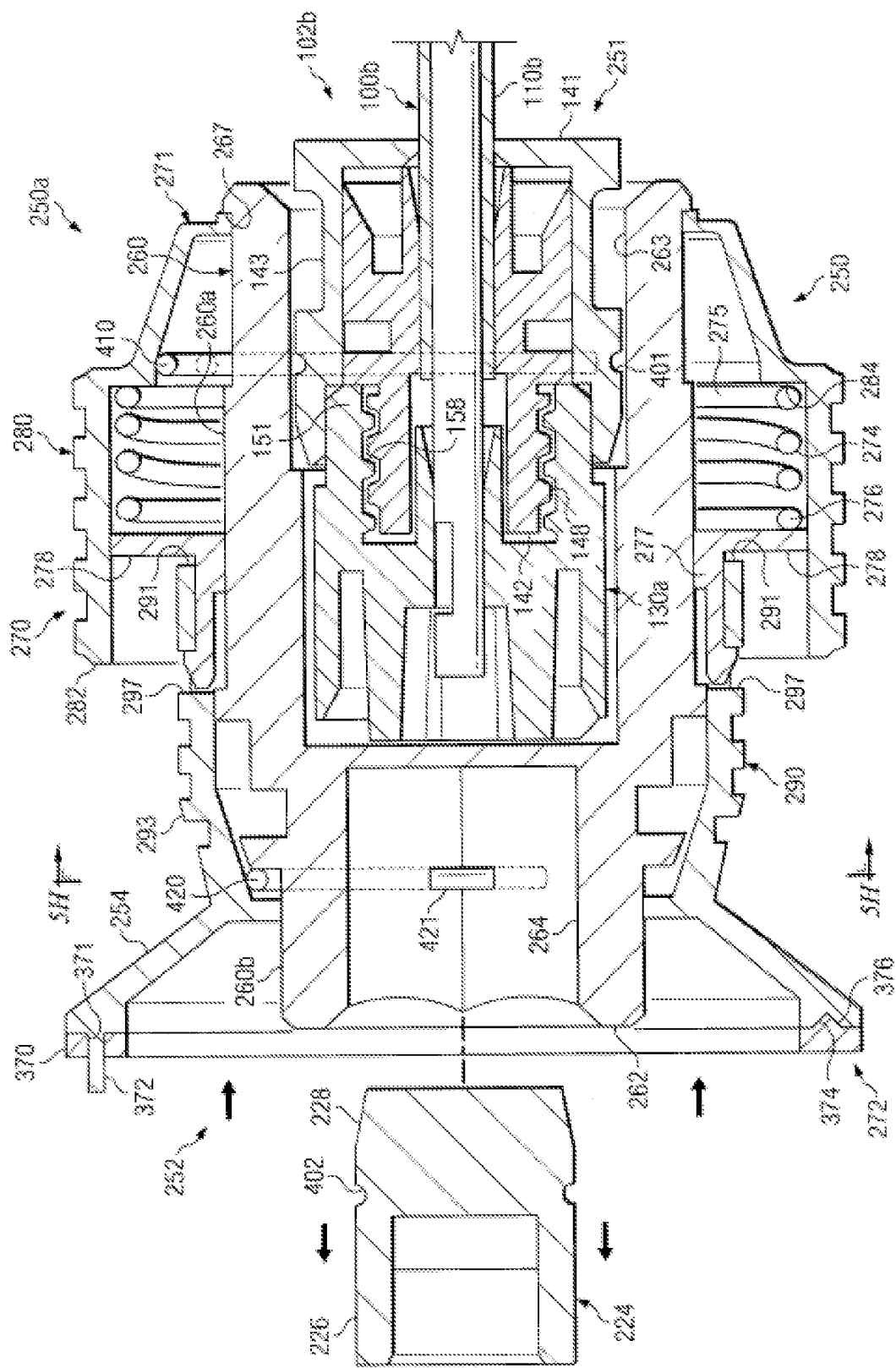
Figure 8A:
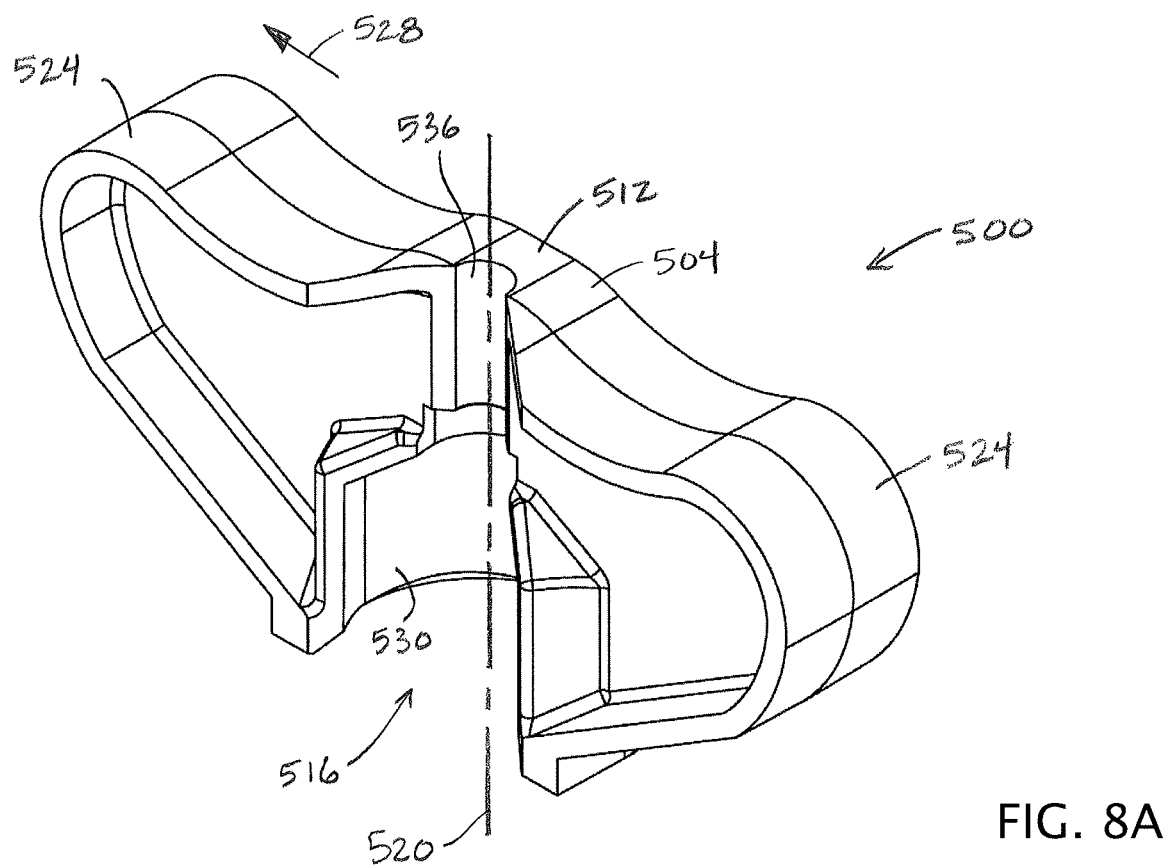
FIGS. 8A-8B depict perspective views of an embodiment of the present assistive devices for removing a biological specimen from an intraosseous device.
Figure 8B:
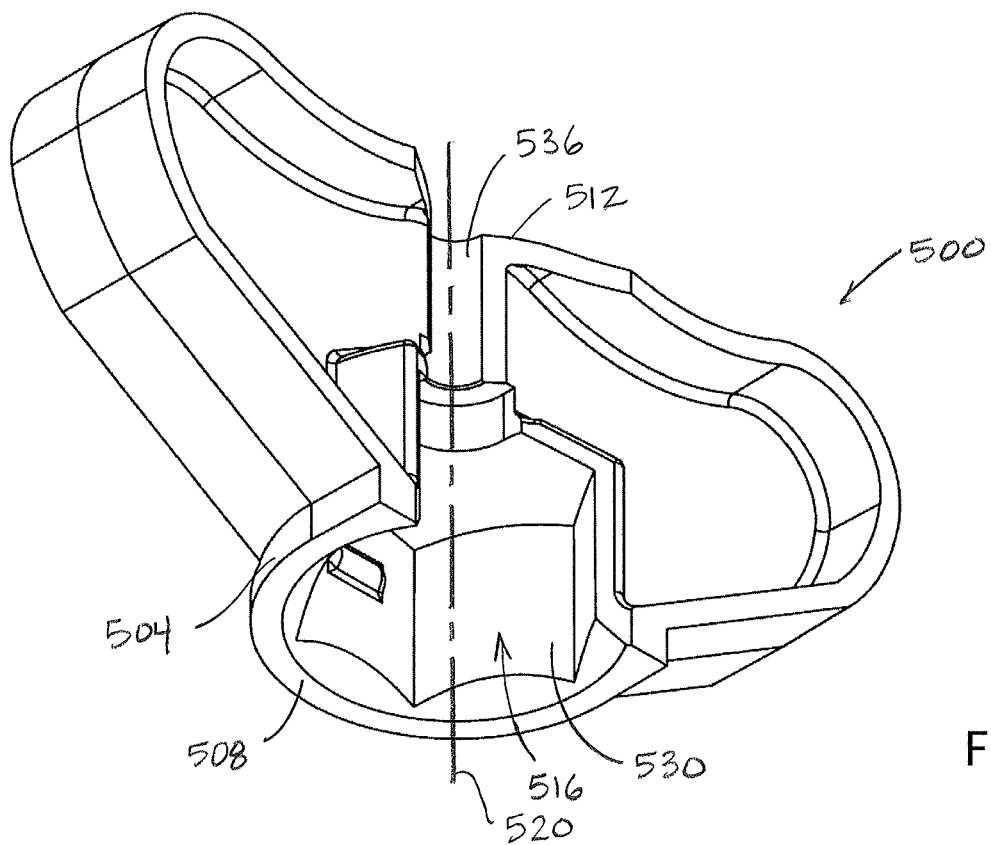
Figure 8C:
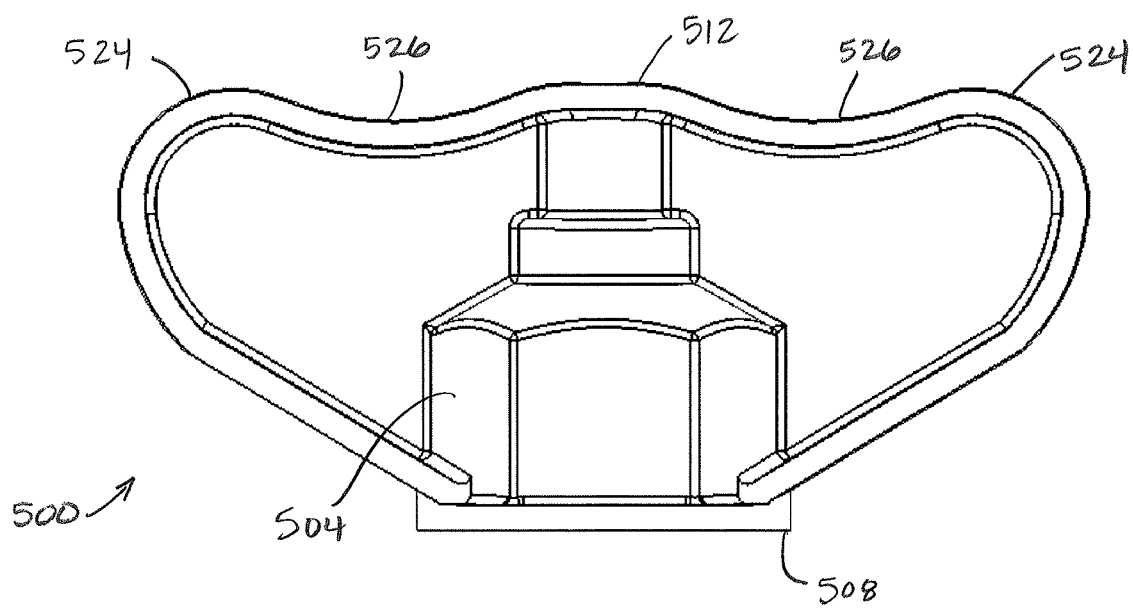
Figure 8D:
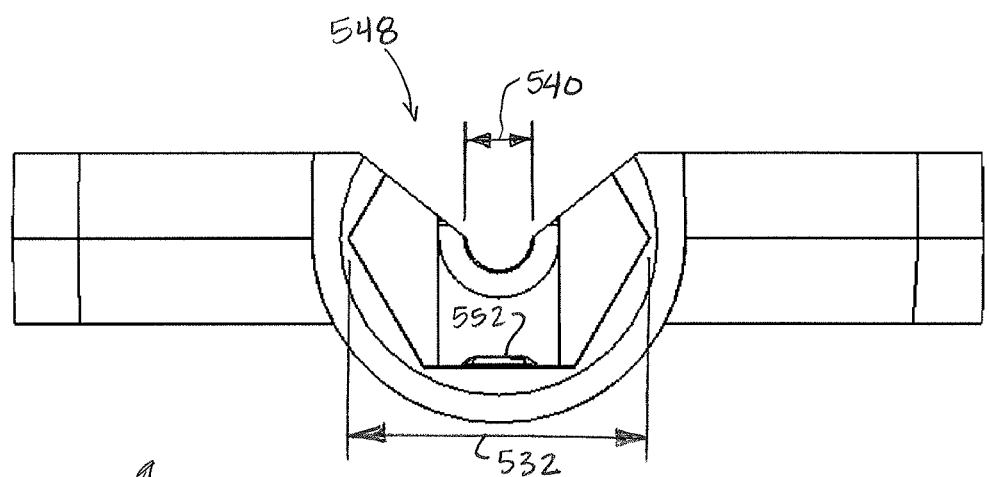

In the embodiment shown, the second end of a hub assembly may be operable to be disposed within a receptacle formed in a coupler assembly, as described in more detail below. One feature of the present disclosure may include forming a hub assembly which may be releasably engaged within a first receptacle disposed in a first end of a coupler assembly (e.g., receptacle 263 proximate first end 261 of elongated core 260 as shown in FIGS. 6A-6B). The dimensions and configuration of receptacle 263 may be selected to prevent rotation of hub 150*a* relative to hub 140*a* if hub assembly 130*a* is disposed in receptacle 263 (e.g., while inserting (rotating) an IO device into a bone and associated bone marrow). A powered driver may be releasably engaged with a second receptacle disposed in a second end of the coupler assembly (e.g., receptacle 264 proximate second end 262 of elongated core 260 as shown in FIGS. 6A-6B).

In the embodiment shown, intraosseous device or aspiration needle set 100*a* includes first end 151 of hub 150*a* spaced from second end 142 of hub 140*a*. Portions of stylet 120 extending from first end 151 of hub 150*a* are shown slidably disposed within lumen or longitudinal bore 118 of cannula 110*a*. Hub assembly 130*a* may include first end 131 which may correspond generally with first end 141 of hub 140*a*. Hub assembly 130*a* may also include second end 132 which may correspond generally with second end 152 of hub 150*a* and second end 102 of hub assembly 130*a*, as shown. Cannula 110*a* may be attached to and extend from first end 141 of hub 140*a*. Second end 142 of hub 140*a* may include one-half a typical Luer lock connection or fitting operable to be releasably engaged with corresponding portions of a Luer lock connection or fitting disposed in first end 151 of second hub 150*a*. For embodiments such as the one shown in FIG. 1A, first end 131 of hub assembly 130*a* may correspond with first end 141 of first hub 140*a*. Second end 152 of second hub 150*a* may correspond with second end 132 of hub assembly 130*a* and second end 102 of aspiration needle set 100*a*.

At least one portion of hub assembly 130*a* may have a generally hexagonal cross section operable to be received within the generally hexagonal cross section of receptacle 263 disposed proximate first end 251 of coupler assembly 250, as shown in FIGS. 6A-6B. For some embodiments, portions of first hub 140*a* disposed adjacent to reduced outside diameter portion 143 may have generally hexagonal cross sections, as shown in FIG. 1A. In other embodiments, various cross sections other than hexagonal may be satisfactorily used to releasably engage a powered driver with one end of a coupler assembly and an intraosseous device with an opposite end of the coupler assembly. Aspiration needle sets may include a trocar, stylet, or penetrator in combination with an associated cannula, catheter or outer penetrator. However, biopsy needles formed in accordance with teachings of the present disclosure may or may not include a trocar, stylet, or inner penetrator.

Hub 140*a* may include second end 142 with opening 144 formed therein. A passageway may extend from second end 142 towards first end 141 of hub 140*a*, as illustrated in FIGS. 6A-6B. A passageway may be operable to communicate fluids with lumen 118 of cannula 100*a*. Second end 142 of hub 140 may include various features of a conventional Luer lock connection or fitting, including threads 148, and corresponding threads 158 may be formed within first end 151 of hub 150*a*, as shown in FIGS. 6A-6B.

For some applications hub 140*a* and hub 150*a* may, for example, be formed using injection molding techniques. For such embodiments hub 140*a* may include reduced outside diameter portion 143 disposed between first end 141 and second end 142. In a similar manner a plurality of void spaces or cutouts 153 may be formed in hub 150*a* adjacent to and extending from second end 152 in the direction of first end 151. The configuration and dimensions of reduced diameter portion 143 and/or cutouts 153 may be varied to optimize associated injection molding techniques and at the same time provide required configurations, dimensions and material strength to allow associated hub assembly 130*a* to function as described in this disclosure.

In some embodiments, tip 123 of stylet 120 may be disposed relatively close to a tip of cannula 110*a*. For some applications, first end 121 of stylet 120 and first end 111*a* of cannula 110*a* may be ground at the same time to form adjacent cutting surfaces. Grinding ends 111*a* and 121 at the same time may result in forming a single cutting unit to form generally matching cutting edges. Other types of cutting surfaces formed in accordance with teachings of the present disclosure may be discussed later (e.g., as described with reference to FIGS. 1B-1D).

Figure 1B:
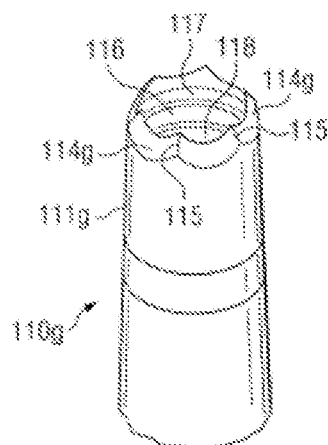
FIG. 1B depicts a perspective view of a second embodiment of the present cannulas.
Figure 1C:
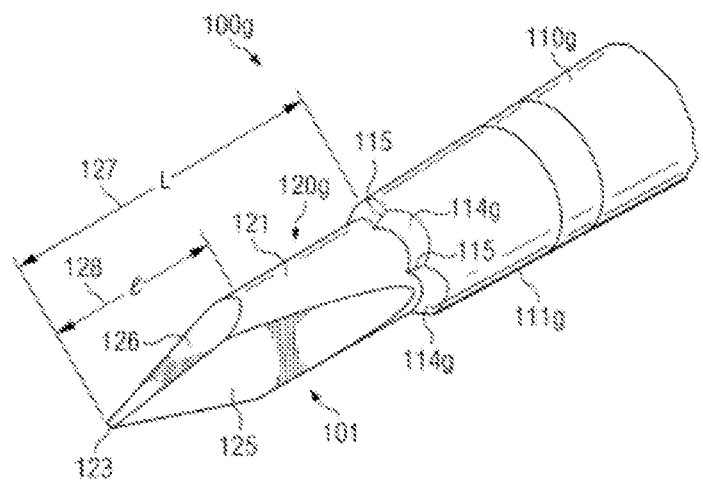
FIGS. 1C and 1D depict perspective views of a second embodiment of the present IO devices having a second embodiment of the present stylets disposed in the cannula of FIG. 2.
Figure 1D:
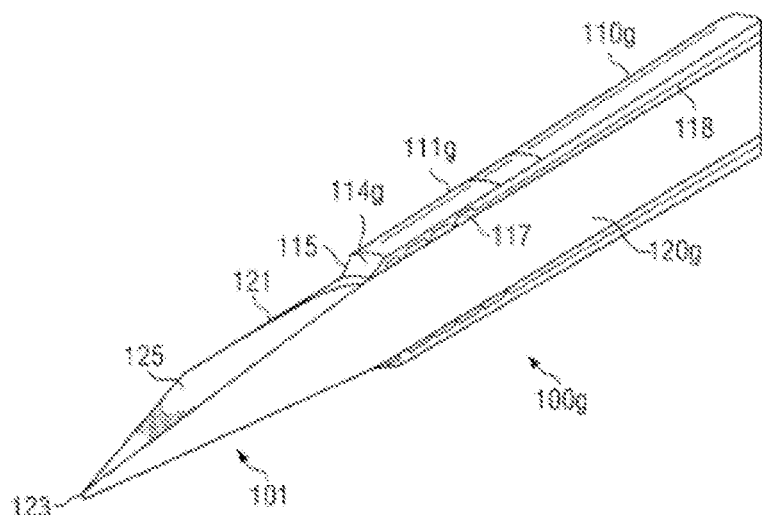

FIGS. 1B-1D show a second example of cutting surfaces and tips which may be formed adjacent to the ends of a cannula and/or an associated stylet in the present embodiments. In the embodiment shown, outer penetrator or cannula 110*g* may include first end 111*g* having a plurality of cutting surfaces 114*g* formed adjacent to opening 116 in first end 111*g*. Opening 116 may communicate with and form a portion of an associated longitudinal bore or lumen 118. For some applications cutting surfaces 114*g* may be formed using electrical discharge machining (EDM) techniques or otherwise, as described in WO 2008/033874. In the embodiment shown, first end 111*g* has a generally tapered configuration or reduced outside diameter as compared with other portions of cannula 110*g*. In other embodiments, first end 111*g* has an outside diameter that is equal to the outside diameter of other portions of cannula 110*g* (e.g., cannula 110*g* can have a constant outside diameter along the entire length of the cannula). Cutting surfaces 114*g* may, for example, be formed using machine grinding techniques. In some embodiments, such as the one shown, end 111*g* of cannula 110*g* may include six ground cutting surfaces 114*g* with respective crowns 115 therebetween. Forming a biopsy needle set and/or biopsy needle with tapered end 111*g* and a plurality of cutting surfaces 114*g* and crowns 115 may provide improved drilling performance (e.g., relative to others configurations) when the resulting biopsy needle set and/or biopsy needle is used with a powered driver in accordance with teachings of the present disclosure. For some applications, a helical groove 117 may be formed within longitudinal bore 118 proximate opening 116. Helical groove 117 may assist with retaining a biopsy specimen or a bone marrow specimen within longitudinal bore 118. For example, a single thread may be disposed within the longitudinal bore or lumen of the cannula such that the helical groove 117 is defined between turns of the thread. Various techniques and procedures may be satisfactorily used to place the single thread or otherwise form the helical groove, as described WO 2008/033874.

As shown in FIG. 1C, a biopsy needle set 100g may include cannula or outer penetrator 110g with stylet or inner penetrator 120g slidably disposed therein. The proximal ends of cannula 110g and stylet 120g may be similar to those of cannula 110a and stylet 120 depicted in FIG. 1A (e.g., may include hubs 140a and 150a, respectively). For some applications first end 101 of biopsy needle set 100g may minimize damage to skin and soft body tissue at an insertion site. For some applications inner penetrator or stylet 120g may include first end 121 having a plurality of cutting surfaces 125 and 126 formed on exterior portions thereof extending from associated tip 123 towards second end of stylet or inner penetrator 120g. For some applications one or more cutting surfaces 125 may be formed having length 127 extending from tip 123 to associated cutting surfaces 114g in associated cannula 110g. One or more cutting surfaces 126 may be formed adjacent to each cutting surface 125 with second length 128. First length 127 may be greater than second length 128. As shown, lengths 127 and 128 are measured parallel to the central longitudinal axis of stylet 120g. The ratio of first length 127 and second length 128 may be varied in accordance with teachings of the present disclosure to provide optimum performance for penetrating a selected bone and associated bone marrow. Additional details of some embodiments of first end 101 are described in WO 2008/033874.

Figure 2:
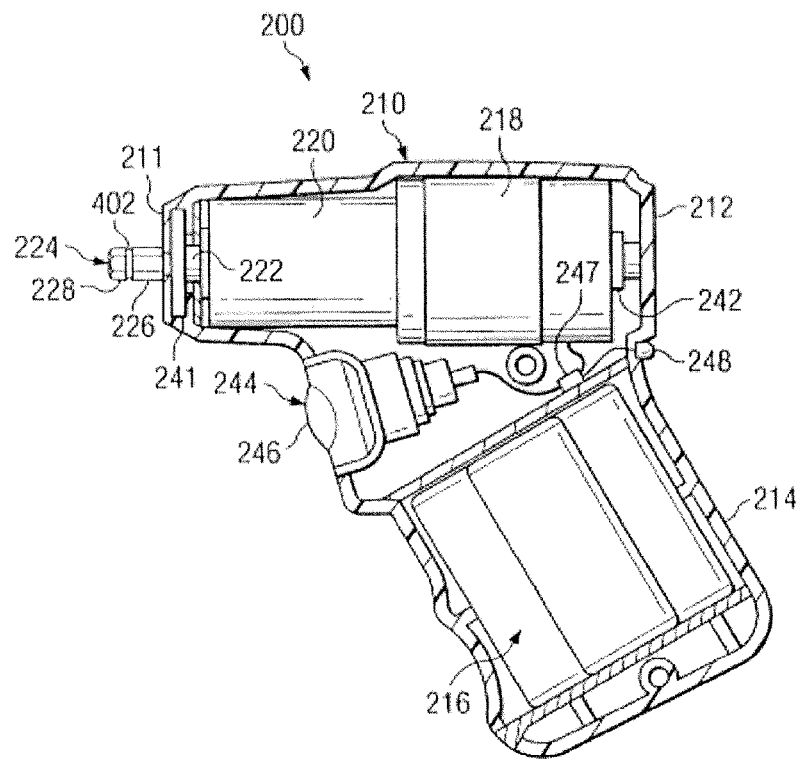
FIG. 2 depicts a cross-sectional side view of one embodiment of the present drivers.

FIG. 2 depicts a cross-sectional view of one embodiment of a driver that can be used with embodiments of the present drivers and kits. In the embodiment shown, powered driver 200 may be used to insert an intraosseous devices into a bone and associated bone marrow. Powered driver 200 may include housing 210 having a general configuration similar to a small pistol defined in part by handle 214. Various components associated with powered driver 200 may be disposed within housing 210 (e.g., handle 214). For example a power source such as battery pack 216 may be disposed within handle 214. Housing 210 may be formed from relatively strong, heavy duty polymeric materials such as polycarbonate or other satisfactory materials. For some applications housing 210 may be formed in two halves (not expressly shown) which may be joined together with a fluid tight seal to protect various components of powered driver 200 disposed therein.

Motor 218 and gear assembly 220 may be disposed within portions of housing 210 adjacent to handle 214. Motor 218 and gear assembly 220 may be generally aligned with each other. Motor 218 may be rotatably engaged with one end of gear assembly 220. Drive shaft 222 may be rotatably engaged with and extend from another end of gear assembly 220 opposite from motor 218. For some applications both motor 218 and gear assembly 220 may have generally cylindrical configurations. Distal end or first end 211 of housing 210 may include an opening with portions of drive shaft 222 extending through the opening, as shown. For some applications, end 224 or the portion of drive shaft 222 extending from first end 211 of housing 210 may have a generally hexagonal cross section with surfaces 226 disposed thereon. Receptacle 263 disposed in second end 252 of coupler assembly 250 may have a matching generally hexagonal cross section, as shown in FIGS. 6A-6C.

Surfaces 226 may extend generally parallel with each other and parallel with respect to a longitudinal axis or rotational axis of drive shaft 222. One or more tapered surfaces 228 may also be formed on end 224 to assist with releasably engaging powered driver 200 with coupler assembly 250. Embodiments of powered driver 200 include speed reduction ratios, for example, of between 60:1 and 80:1, resulting in drive shaft RPMs that are reduced relative to motor RPMs. Coupler assemblies having corresponding openings or receptacles may be releasably engaged with end 224 extending from first end 211 of powered driver 200. For example, end 224 extending from first end 211 of housing 210 may be releasably engaged with receptacle 264 disposed proximate second end 252 of coupler assembly 250, as shown in FIGS. 6A-6B.

For some applications thrust bearing 241 may be disposed between first end or distal end 211 of housing 210 and adjacent portions of gear assembly 220. Thrust bearing 242 may be disposed between second end or proximal end 212 of housing 210 and adjacent portions of motor 218. Thrust bearings 241 and 242 may limit longitudinal movement of motor 218, gear assembly 220 and drive shaft 222 within associated portions of housing 210. Trigger assembly 244 may also be disposed within housing 210 proximate handle 214. Trigger assembly 244 may include trigger or contact switch 246. Motor 218 may be energized and deenergized by alternately depressing and releasing trigger 246. Electrical circuit board 247 may also be disposed within housing 210. Electrical circuit board 247 may be electrically coupled with trigger assembly 244, motor 218, power supply 216 and indicator light 248. For some applications indicator light 248 may be a light emitting diode (LED) or a small more conventional light bulb. For some applications indicator light 248 may be activated when ninety percent (90%) of electrical storage capacity of battery pack 216 has been used. The configuration and dimensions of an intraosseous device formed in accordance with teachings of the present disclosure may vary depending upon respective intended applications for each intraosseous device. For example the length of a biopsy needle formed in accordance with teachings of the present disclosure may vary from approximately five (5) millimeters to thirty (30) millimeters.

Coupler assemblies incorporating teachings of the present disclosure may function as "quick release mechanisms" operable to engage and disengage an IO device from a powered driver (e.g., a driver disposed within a flexible containment bag or sterile sleeve). Such coupler assemblies may allow rotation of an IO device (e.g., biopsy needle or needle set) without damage to the flexible containment bag or sterile sleeve. One end of the coupler assembly may be operable to form a fluid seal or fluid barrier with adjacent portions of the containment bag or sterile sleeve. A coupler assembly incorporating teachings of the present disclosure may also be described as a port assembly attached to a containment bag. Such port assemblies may allow easy engagement or disengagement of a powered driver from an IO device and at the same time allow the powered driver to "power in and power out" an IO device from an insertion site.

Figure 3:
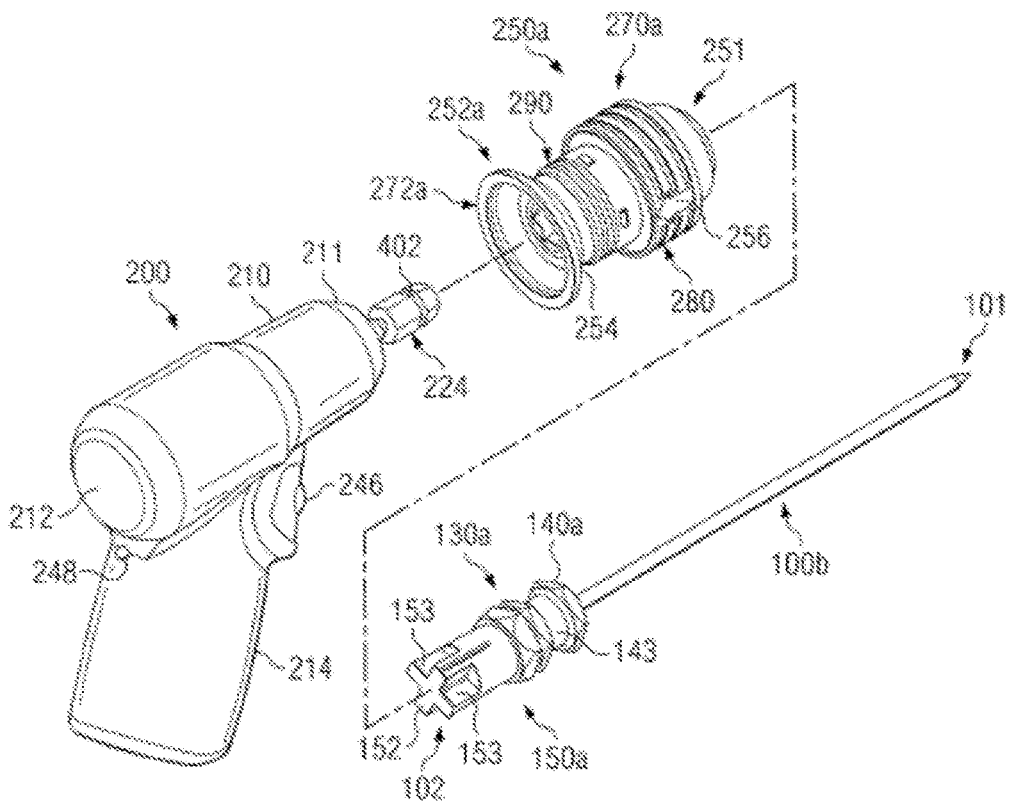
FIG. 3 depicts a perspective view of the driver of FIG. 2 with a corresponding coupler assembly and a third embodiment of the present IO devices.
Figure 4:
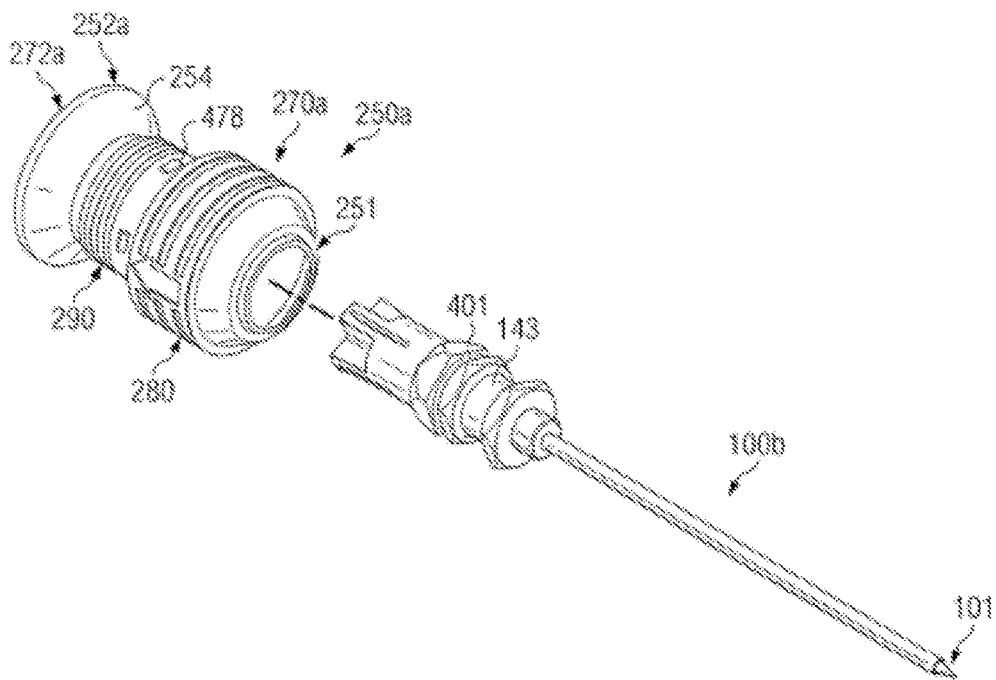
FIG. 4 depicts the coupler assembly and IO device of FIG. 3.
Figure 5:
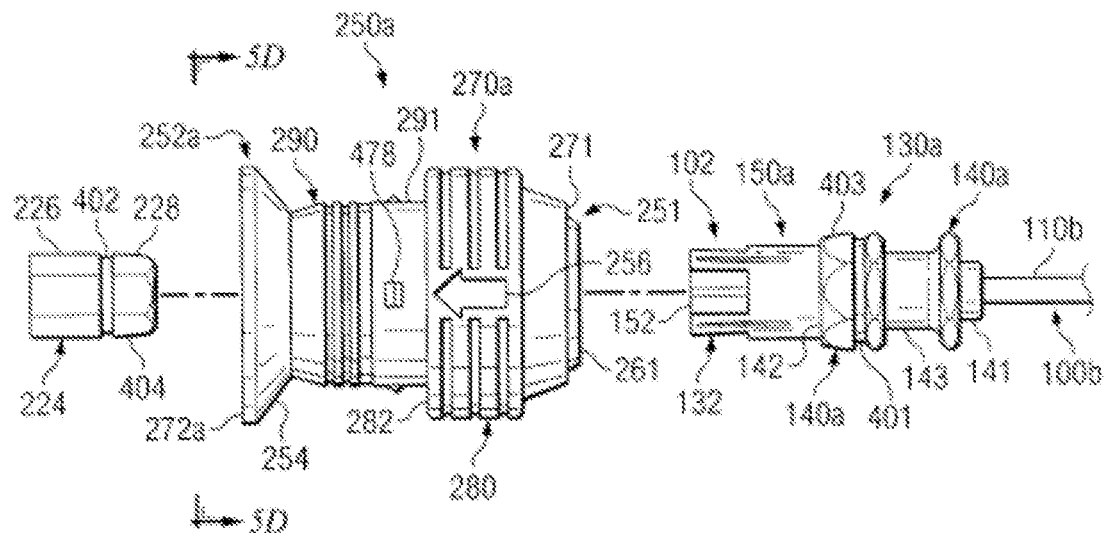
FIG. 5 depicts portions of the driver, coupler assembly, and IO device of FIG. 3.

FIGS. 3-6C depict an example of a coupler assembly 250 suitable for some embodiments of the present assemblies and kits. FIGS. 3-5 are perspective views showing various views of powered driver 200, coupler assembly 250a, and intraosseous device 100b that is substantially similar to device 100a with the exception that device 100b does not include markings 104. Coupler assembly 250a includes a first end 251 operable to be releasably engaged with one end of an intraosseous device such as, but not limited to, second end 102 of biopsy needle set 100b. Coupler assembly 250a also includes a second end 252 operable to be releasably engaged with a portion of a drive shaft extending from a powered driver, such as, but not limited to, end 224 of drive shaft 222 extending from first end 211 of housing 210 of powered driver 200. Though not depicted here, second end 252 of coupler assembly 250 may be securely engaged with an opening in a containment bag or sterile sleeve, as described in WO 2008/033874.

Coupler assemblies incorporating various teachings of the present disclosure may be placed in a medical procedure tray or kit with one end down and an opposite end looking up to allow "hands free" releasable engagement with a powered driver or a manual driver. For example, coupler assembly 250a may be disposed in medical procedure tray with first end 251 facing downward and second end 252 facing up such that end 224 of drive shaft 222 (of driver 200) may be inserted into and releasably engaged with second end 252 of coupler assembly 250 without requiring an operator or user to physically contact or manipulate any portion of coupler assembly 250a. As described below, coupler 250a may include a "hands free" latching mechanism.

In the embodiment shown, coupler assembly 250a may include elongated core 260 with housing assembly 270 slidably disposed on exterior portions of elongated core 260. Housing assembly 270/270a may include first end 271 and second end 272 which may be generally aligned with respective first end 261 and respective second end 262 of elongated core 260. For some applications, elongated core 260 may have a generally cylindrical configuration defined in first exterior portion 260a and second exterior portion 260b with various shoulders and/or recesses formed thereon. For some embodiments first exterior portion 260a may have a larger diameter than second exterior portion 260b. Housing assembly 270 may be described as having a generally hollow, cylindrical configuration defined in part by first housing segment 280 and second housing segment 290. The first end of housing segment 280 may generally correspond with first end 271 of housing assembly 270. The second end of second housing segment 290 may generally correspond with second end 272 of housing assembly 270. First end 291 of second housing segment 290 may be described as having a generally cylindrical configuration with an outside diameter smaller than the adjacent inside diameter of second end 282 of first housing segment 280. Second housing segment 290 may slide longitudinally from a first position (FIG. 6A) to a second position (FIG. 6B) within second end 282 of first housing segment 280 to release one end of a drive shaft engaged with second end 252 of coupler assembly 250.

A biasing mechanism such as coiled spring 274 may be disposed around exterior portion 260a of generally elongated core 260. First end 275 of coiled spring 274 may contact annular shoulder 284 formed on interior portions of first housing segment 280. Second end 276 of coiled spring 274 may contact annular shoulder 278 disposed proximate first end 291 of second housing segment 290. Coil spring 274, annular shoulder 284 and annular shoulder 278 may cooperate with each other to generally maintain first housing segment 280 and second housing segment 290 in a first extended position relative to each other. Other biasing mechanisms such as, but not limited to, leaf springs and bellows (not expressly shown) may also be disposed between annular shoulder 284 and annular shoulder 278. Annular shoulder 278, associated with second end 276 of coiled spring 274, may extend radially outward from generally cylindrical ring 277. Generally cylindrical ring 277 may be slidably and rotatably disposed on exterior portion 260a of elongated core 260. Annular shoulder 279 may be disposed on interior portions of generally cylindrical ring 277 and may extend radially inward toward adjacent portions of elongated core 260. Annular shoulder 268 may be formed on exterior portion 260a of elongated core 260 intermediate first end 261 and second end 262. The configuration and dimensions of annular shoulder 268 and annular shoulder 279 are selected to be compatible with each other such that engagement between annular shoulder 279 of generally cylindrical ring 277 with annular shoulder 268 of elongated core 260 may limit movement of second housing segment 290 longitudinally in the direction of second end 262 of elongated core 260.

For some applications a plurality of flexible collets or fingers 477 may extend from generally cylindrical ring 277 opposite from annular shoulder 278. Respective collet heads 478 may be formed on the end of each collet 477 opposite from annular shoulder 278. The dimensions and configuration of collet heads 478 may be selected to be received within respective slots or openings 297 formed in second housing 290. During manufacture of coupler assembly 250a, each collet head 478 may be disposed within respective slot or opening 297 to securely engage generally cylindrical ring 277 and annular shoulder 278 proximate first end 291 of second housing segment 290. As a result, second housing segment 290 and annular shoulder 278 may generally move as a single unit relative to elongated core 260 and first housing segment 280. During disengagement of an intraosseous device from first end 251 of coupler assembly 250a, first housing segment 280 may move or slide longitudinally toward second housing segment 290. In a similar manner, second housing segment 290 may move or slide longitudinally toward first housing segment 280 during disengagement of a powered driver from second end 252 of coupler assembly 250a.

Annular shoulder 267 may be formed on exterior portions of elongated core 260 proximate first end 261. Annular shoulder 267 may engage portions of first end 271 of housing 270 to limit longitudinal movement of first housing segment 280 during longitudinal movement of second housing segment 290 towards first end 261 of elongated core 260 during disengagement of a powered driver from second end 252 of coupler assembly 250a. As previously noted, annular shoulder 268 may be formed on exterior portions of elongated core 260 between first end 261 and second end 262. Engagement between annular shoulder 268 and annular shoulder 279 of generally cylindrical ring 277 may limit movement of second housing segment 290 toward second end 262 of elongated core 260. Contact between spring 274 and annular shoulder 278 and annular shoulder 284 of first housing segment 280 may limit the longitudinal movement of first housing segment 280 in the direction of second end 262 of elongated core 260 during disengagement of an intraosseous device from first end 251 of coupler assembly 250a.

Generally cylindrical ring 277 and attached annular shoulder 279 may slide longitudinally on exterior portions of annular core 260 between annual shoulder 268 and annular shoulder 267. First housing segment 280 may move longitudinally toward second end 262 of elongated core 260 to release one end of intraosseous device from engagement with first end 251 of coupler assembly 250a. In a similar manner, second housing segment 290 may move longitudinally toward first end 261 of elongated core 260 to release one end of a drive shaft extending from a powered driver engaged with second end 252 of coupler assembly 250a. A wide variety of latches and latch mechanisms may be satisfactorily used to releasably engage one end of an intraosseous device within a first end of a coupler assembly incorporating teachings of the present disclosure. In a similar manner, a wide variety of latches and latch mechanisms may be satisfactorily used to releasably engage one end of a drive shaft extending from a powered driver or manual driver within a second end of the coupler assembly incorporating teachings of the present disclosure.

For embodiments represented by coupler assembly 250a, first latch 410 may be disposed on exterior portions of elongated core 260 proximate receptacle 263 adjacent to first end 261 to releasably engage one end of an IO device such as second end 102 of biopsy needle set 100b within receptacle 263 of coupler assembly 250a. Second latch mechanism 420 may be disposed on exterior portions of elongated core 260 proximate receptacle 264 adjacent to second end 262 to releasably engage one end of a drive shaft with second end 252 of coupler assembly 250a. Second latch 420 may be used to releasably engage one portion of a drive shaft such as end 224 of drive shaft 222 extending from powered driver 200 within second end 252 of coupler assembly 250a. Latch 410 may releasably engage an intraosseous device with first end 251 of coupler assembly 250a and substantially the same latch 420 may releasably engage a powered driver with second end 252 of coupler assembly 250a.

For some applications, latches 410 and 420 may have similar configurations such as a general "omega" shape (e.g., latch 420). However, latch 410 may have larger dimensions corresponding generally with exterior portion 260a of elongated core 260. Latch 420 may have smaller dimensions corresponding generally with exterior portion 260b of elongated core 260. Various features of the present disclosure may be described with respect to latch mechanism 420 along with adjacent portions of second housing segment 290 and exterior portion 260b of elongated core 260. Respective detents 421 and 422 may be formed on opposite ends of generally omega shaped latch 420. In a similar manner, respective detents (not expressly shown) may be formed on the ends of generally omega shaped latch 410. The configuration and dimensions of detents 421 and 422 may be compatible with placing each detent 421 and 422 in a respective slot or opening extending between exterior portion 260b of elongated core 260 to interior portions of receptacle 264 disposed proximate second end 252 of coupler assembly 250a. Latch 420 may have a first position in which portions of detents 421 and 422 may extend through the respective slots. The dimensions and configuration of detent 421 and 422 may be operable to be securely engaged with annular groove 402 formed in end 224 of powered driver 200. In a similar manner, respective detents on associated latch 410 may be releasably engaged with annular groove 401 disposed in second end 102 of biopsy needle 100b. For some applications, a plurality of tapered surfaces 403 may be formed on exterior portions of hub 140a proximate first end 142 to radially expand detent mechanisms associated with omega shaped latch 410 radially outward while inserting second end 102 of biopsy needle 100b into first end 251 of coupler assembly 250a. The detent mechanism may "snap" into annular groove 401 when aligned therewith. In a similar manner, a plurality of tapered surfaces 228 may be formed on exterior portions of end 224 of drive shaft 222 extending from powered driver 200 to radially expand detent mechanisms 421 and 422 radially outward during the insertion of end 224 of powered driver 200 into second end 252 of coupler assembly 250a.

Detent mechanisms 421 and 422 will "snap" into annular groove 402 when aligned therewith.

Engagement between detent mechanisms associated with latch 410 with annular groove 401 of hub assembly 130a will generally retain second end 102 of biopsy needle 100b securely engaged with first end 251 of coupler assembly 250a. This engagement may allow powered driver 200 to rotate or spin cannula or biopsy needle 110b while withdrawing cannula or biopsy needle 110b from an insertion site. In a similar manner, engagement between detent mechanisms 421 and 422 of omega shaped latch 420 and annular groove 402 of end 224 of powered driver 200 will generally retain second end 252 of coupler assembly 250a engaged with powered driver 100 during withdrawal of cannula 110b from an insertion site.

Biopsy needle set 100b may be released from first end 251 of coupler assembly 250a by sliding first housing segment 280 longitudinally toward second end 262 of elongated core 260. Such movement of first housing segment 280 will result in interior tapered surface 286 contacting exterior portions of omega shaped latch 410 and compressing omega shaped latch 410 to radially expand associated detent mechanisms (not expressly shown) from engagement with annular groove 401 of hub assembly 130a. As a result, biopsy needle set 100b may be easily withdrawn from first end 251 of coupler assembly 250a. In a similar manner, longitudinal movement of second housing segment 290 toward first end 251 of coupler assembly 250a will result in interior tapered surface 296 contacting exterior portions of omega shaped latch 420 to compress generally omega shaped latch 420 and withdraw or retract detent mechanisms 421 and 422 from engagement with annular groove 402 of end 224. As a result, powered driver 200 and second end 222 of coupler assembly 250a may be easily disconnected from each other.

Flange 254 may be generally described as having an enlarged funnel shaped or bell shaped configuration. The dimensions and configuration of flange 254 may be selected to be compatible with end 211 of powered driver 200. As previously noted, coupler assembly 250a may be securely engaged with an opening formed in a containment bag or sterile sleeve in accordance with teachings of the present disclosure. For embodiments such as the one shown, end 272 of housing 270 of coupler assembly 250a may include annular ring 370 operable to be securely engaged with adjacent portions of flange 254. The outside diameter of annular ring 370 may generally correspond with the outside diameter of adjacent portions of flange 254. The inside diameter of annular ring 370 may also generally correspond with the inside diameter of adjacent portions of flange 254. For some embodiments a plurality of posts 372 and generally V shaped grooves 374 may be alternatingly disposed on the extreme end of flange 254. Annular ring 370 may include a plurality of holes 371 sized to received respective posts 372 therein. Annular ring 370 may also include a plurality of generally V shaped projections 376 sized to be received within respective generally V shaped grooves 374 formed in adjacent portions of flange 254. For embodiments such as the one shown, portions of a containment bag (e.g., around an opening) may be disposed between annular ring 370 and adjacent portions of flange 254. For example, post 372 may be inserted through a corresponding hole in a containment bag adjacent to the perimeter of an opening in the containment bag. Holes 371 in annular ring 370 may be aligned with respective posts 372. Other portions of a containment bag (e.g., adjacent to an opening) may be trapped between respective V shaped projections 376 and V shaped grooves 374. Various welding techniques including, but not limited to, laser welding may be applied to posts 372 to bond annular ring 370 with adjacent portions of flange 354. As a result, a perimeter of a containment bag around an opening in the containment bag may be securely engaged with second end 252 of coupler assembly 250*a*.

Figure 7:
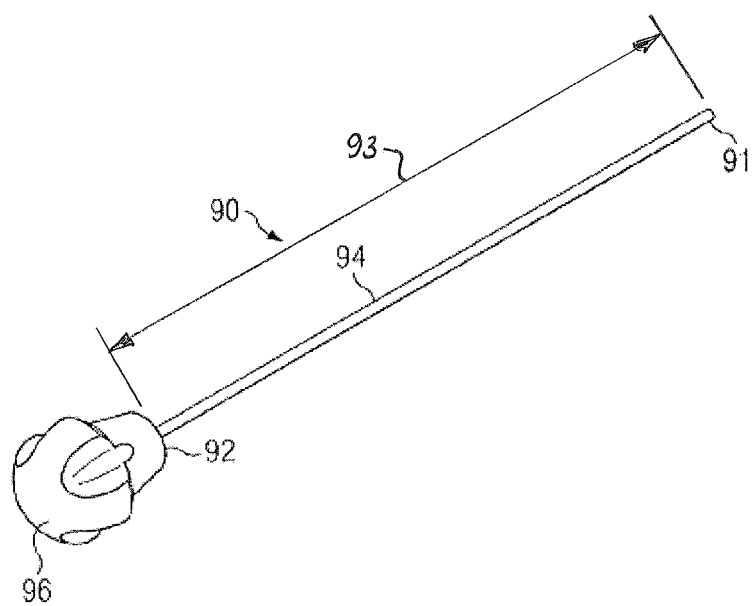
FIG. 7 illustrates an example of an ejector suitable for use with the present cannulas.

FIG. 7 shows an example an ejector or ejector rod 90 that may be used to remove a biopsy specimen from a generally hollow cannula or biopsy needle (e.g., 110*a*) after inserting a first end of the generally hollow cannula or biopsy needle into a bone and/or associated bone marrow. In the embodiment shown, ejector 90 comprises a head or handle 96 and an elongated member or rod 94 extending from head 96 to a distal end 91 and spaced from the head (e.g., from a distal side 92 of the head) by a length 93 that is at least as large as a length of a channel or lumen in an intraosseous device (or portion of an intraosseous device) with which ejector 90 is configured to be used. For example, where ejector 90 is configured to be used with cannula 110*a*, length 93 may be greater than the length from second end 142 of hub 140*a* to first end 101 of cannula 110*a*. Similarly, the dimensions and configuration of first end 91 of elongated member 90 may be selected to be compatible with inserting first end 91 through an opening in the second end of an associated biopsy needle (e.g., through opening 144 in hub 140*a*) and through a lumen or channel defined by the needle (e.g., through the lumen defined through cannula 110*a*).

FIGS. 8A-8F depict various views of an embodiment 500 of the present apparatuses or assistive devices for assisting with removal of a biological sample from an intraosseous device (e.g., 100*a*). In the embodiment shown, apparatus 500 comprises: a body 504 that includes a first end 508 and a second end 512. Body 504 defines a channel 516 that has a longitudinal axis 520, and that is configured to removably receive a portion of a cannula (e.g., 110*a*) of an intraosseous device that also includes a hub (e.g., 140*a*) while preventing passage of the hub through the channel. Body 504 also includes at least one protrusion 524 (e.g., two, as shown) each extending laterally (e.g., in a direction 528 perpendicular to axis 520) outward relative to axis 520, as shown. In the embodiment shown, each protrusion 524 defines a gripping surface 526 facing away from first end 508 of body 504, as shown. In the embodiment shown, gripping surfaces 526 are curved to resist slippage of a user's fingers. In other embodiments, gripping surfaces 526 may be knurled or otherwise textured and/or configured to resist slippage of a user's fingers during use.

In the embodiment shown, channel 516 includes a first portion 530 having a first transverse dimension 532, a second portion 536 disposed between first portion 530 and second end 512 and having a second transverse dimension 540 that is smaller than first transvers dimension 532. In this embodiment, channel 516 is configured to receive a portion of an intraosseous device (e.g., 100*a*) having a hub (e.g., 140*a*) and a cannula (e.g., 110*a*) extending from the hub, with first portion 530 receiving a part of the hub (e.g., 140*a*), and second portion 536 receiving a part of the cannula (e.g., 110*a*) while preventing passage of the hub through the second portion (e.g., via a shape and/or transverse dimension(s) of second portion 536 that are too small or otherwise physically incompatible with passage of the hub through second portion 536 along axis 520). In the embodiment shown, first portion 530 has a non-circular cross-sectional shape configured to prevent rotation of a hub (e.g., 140*a*) of an intraosseous device (e.g., 100*a*) relative to body 504 when the portion of the intraosseous device is disposed in channel 516. For example, the depicted embodiment is configured for use with an intraosseous device having an equilateral polygonal (e.g., hexagonal) hub (e.g., 140*a*) and first portion 530 has a corresponding cross-sectional shape (e.g., defined by a plurality of planar surfaces 544, as shown) configured to prevent rotation of the hub when the hub is disposed in first portion 530. In the embodiment shown, a lateral portion 548 of channel 516 is open between first end 508 and second end 512, as shown, such that an intraosseous device can be laterally inserted into channel 516 rather than requiring a distal end of an intraosseous device (e.g., first end 111*a* of cannula 110*a*) to be inserted through first end 508 of body 504. As such, in the depicted embodiment, body 504 does not include six sides (because one side of what would otherwise be a closed hexagonal cross-sectional shape is omitted to permit lateral insertion of a cannula), but the cross-sectional shape of first portion 530 still corresponds to an equilateral hexagon (e.g., such as the one that defines the cross-sectional perimeter of hub 140*a*). In other embodiments, channel 516 may have a closed cross-section along all or part of its length between first end 508 and second end 512.

Figure 11:
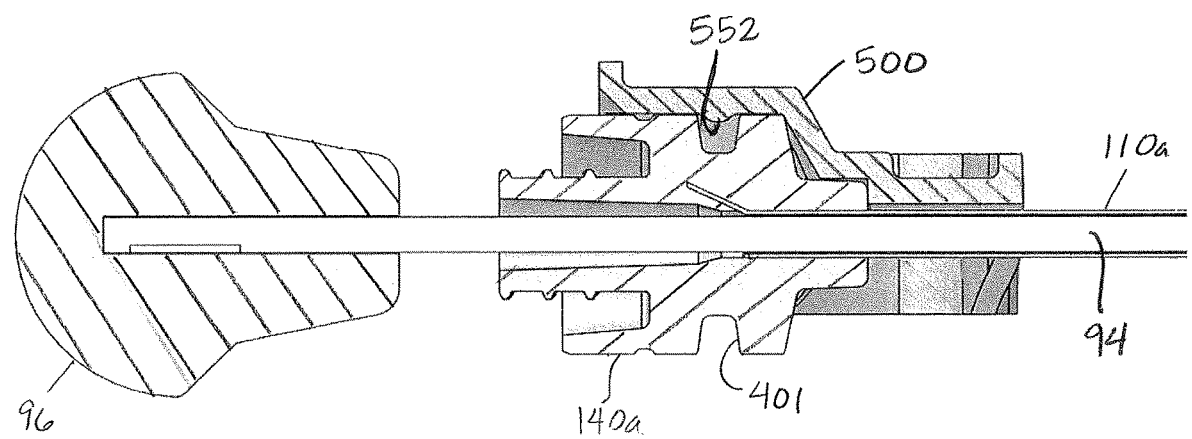
FIG. 11 depicts an enlarged side view of the head of the ejector of FIG. 7 and the assistive device of FIGS. 8A-8B during operation to push a biological sample out of the distal end of the cannula of an intraosseous device.

In the embodiment shown, body 504 further includes a protrusion 552 that extends into first portion 530 of channel 516, as shown, and that is configured to extend into a recess in a hub of an intraosseous device (e.g., an annular recess extending around a longitudinal axis of the hub, such as, for example, annular groove 401 of hub 140*a*) that is disposed in the channel to resist movement of the intraosseous device away from second portion 536 (e.g., as shown in FIG. 11).

Figure 9A:
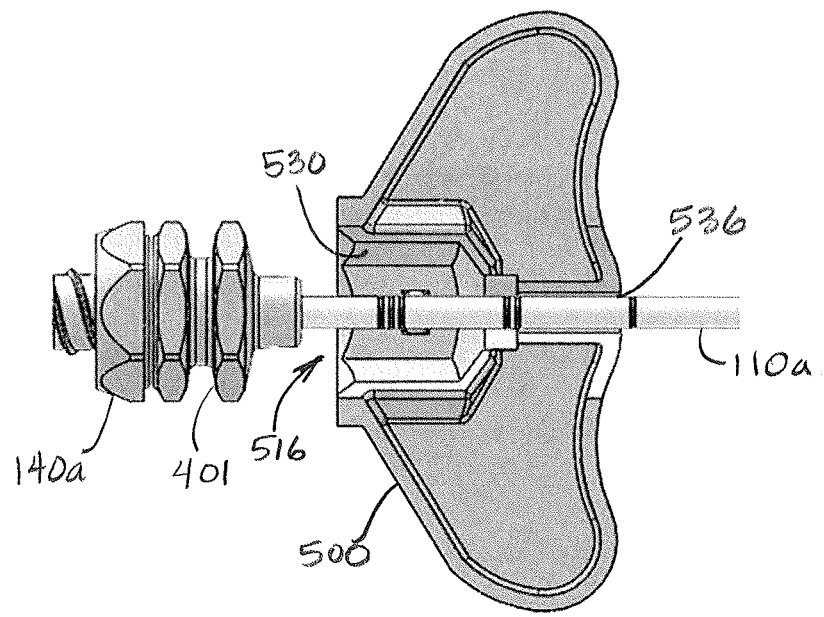
FIGS. 9A-9B depict enlarged side views illustrating assembly of the assistive device of FIGS. 8A-8B with an intraosseous device and the ejector of FIG. 7.
Figure 9B:
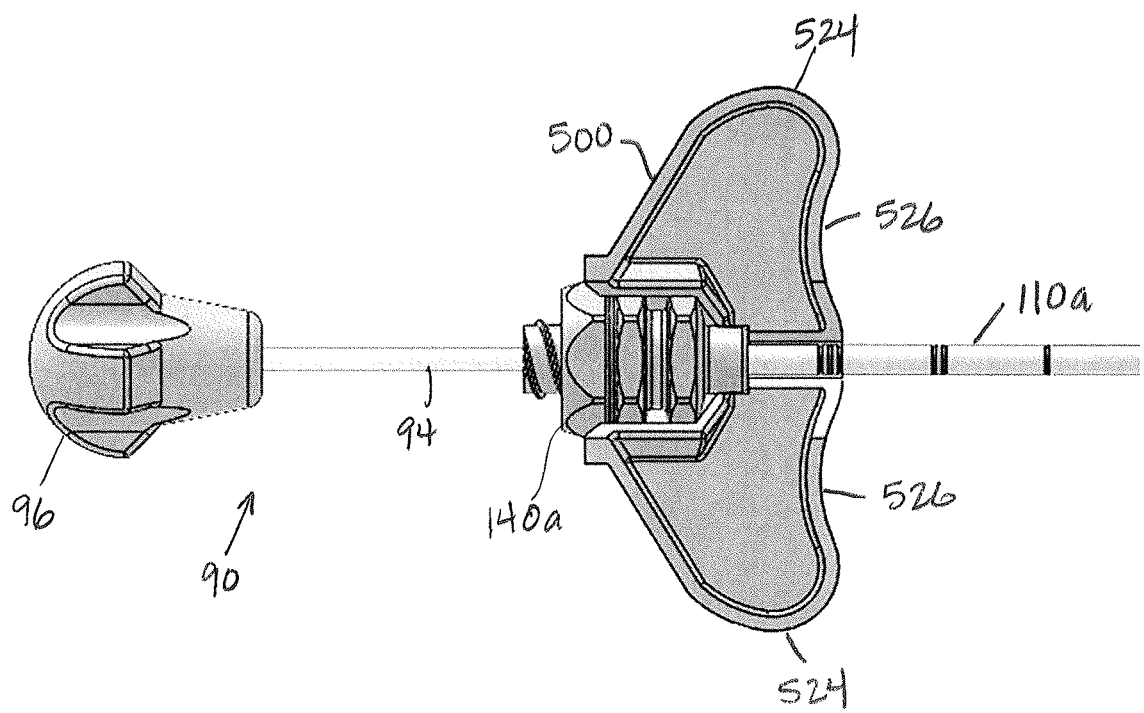

FIGS. 9A-9B, 10A-10C, and 11 illustrate an example of the assembly and operation of device 500 with a portion (cannula 110*a* and hub 140*a*) of intraosseous device 100*a* and the ejector 90. As illustrated in FIG. 9A, the portion of the intraosseous device can be disposed in channel 516 of device 500 by laterally inserting cannula 110*a* into channel 516 with hub 140*a* outside of channel 516. Hub 140*a* can then be longitudinally advanced in direction 556 toward device 500 such that hub 140*a* is received in second portion 536 of channel 516, as shown in FIG. 9B. Elongated member 94 of ejector 90 can then be inserted into opening 144 of hub 140*a*, and distal end 91 advanced (to push a biological sample 600 in cannula 110*a*) toward first end 111*a* of the cannula. As shown in FIG. 11, head 96 of ejector 90 and protrusions 524 can be pushed together (e.g., head 96 pushed toward protrusions 524). For example, when hub 140*a* is seated or received in device 500 and ejector 90 is inserted into cannula 110*a* through hub 140*a*, as shown in FIG. 9B, a user can place head 96 of ejector 90 into the user's palm and can extend the user's fingers of the same hand around projections 524 (e.g., contacting gripping surfaces 526) and squeeze to cause head 96 to advance in direction 556 toward device 500, as shown in FIG. 11.

In some embodiments, device 500 can also be used as a handle to assist with manipulating an intraosseous device (e.g., 100*a*, 100*g*) during insertion of the intraosseous device and/or while obtaining a tissue (e.g., bone marrow) sample from a patient.

Embodiments of the present kits can comprise an embodiment of the present ejectors (e.g., 90) and an embodiment of the present assistive devices (e.g., 500). Some embodiments of the present kits can further comprise an embodiment of the present intraosseous devices (e.g., 100*a*, 100*g*), an embodiment of the present couplers (e.g., 250*a*), and/or an embodiment of the present drivers (e.g., 200). Some embodiments of the present kits are sterile.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A kit comprising:
    an intraosseous device comprising:
        a hub having a first end, a second end, and an opening extending from the first end to the second end; and
        a cannula extending from the second end of the hub to a distal end spaced from the hub by a first length, the cannula defining a lumen in fluid communication with the opening of the hub;
    an ejector comprising:
        a head; and
        an elongated member extending from the head to a distal end spaced from the head by a second length at least as large as the first length, the elongated member configured to be inserted into the lumen of the cannula; and
    an assistive device comprising a body including a first end and a second end, the body defining a channel having a longitudinal axis and configured to removably receive a portion of the cannula and prevent passage of the hub through the channel, the body further including at least one projection extending laterally outward relative to the longitudinal axis of the channel, and the channel further including a first portion having a first transverse dimension and configured to prevent rotation of the hub when a part of the hub is disposed in the first portion;
    where the assistive device is configured to removably receive the portion of the cannula in the channel of the assistive device such that, if the elongated member is inserted into the lumen of the cannula through the opening in the hub, the head and assistive device can be pushed together to cause the distal end of the elongated member to push a biological sample through the distal end of the cannula;
    where the hub of the intraosseous device includes an annular groove extending around a longitudinal axis of the hub, and where the body of the assistive device includes a protrusion defined by a bump formed on an inner surface of the body and extending from the inner surface of the body into the first portion of the channel, the bump fixed relative to the first portion of the channel and configured to extend into the annular groove of the hub to resist movement of the intraosseous device away from the assistive device when the portion of the cannula of the intraosseous device is received in the channel of the assistive device; and
    where a lateral portion of the channel between the first end of the body and the second end of the body is configured to laterally receive the intraosseous device, and where the lateral portion of the channel is configured to prevent laterally inserting the hub into the channel, such that the intraosseous device can be disposed in the channel by laterally inserting the cannula into the channel with the hub outside of the channel and then longitudinally advancing the hub in a direction toward the body such that the hub is received in the channel.

2. The kit of claim 1, where the channel further includes a second portion disposed between the first portion and the second end of the body and having a second transverse dimension that is smaller than the first transverse dimension, the longitudinal axis of the channel extends through the first portion and the second portion, and the channel is configured to receive a portion of the intraosseous device with the first portion of the channel receiving the part of the hub, and the second portion of the channel receiving a part of the portion of the cannula while preventing passage of the hub through the second portion.

3. The kit of claim 2, where the hub of the intraosseous device has a non-circular perimeter and the first portion of the channel in the assistive device is shaped to prevent the rotation of the hub relative to the assistive device when the portion of the intraosseous device is disposed in the channel.

4. The kit of claim 3, where the first portion of the channel is defined by a plurality of planar surfaces configured to prevent the rotation of the hub relative the assistive device when the part of the hub is disposed in the first portion of the channel of the assistive device.

5. The kit of claim 1, where each projection of the assistive device defines a gripping surface facing away from the first end of the body of the assistive device.

6. The kit of claim 1, where the protrusion is integrally formed with the body of the assistive device.

7. An apparatus for assisting with removal of a biological sample from an intraosseous device, the apparatus comprising:
    a body including a first end and a second end, and defining a channel with a first portion having a first transverse dimension, a second portion disposed between the first portion and the second end and having a second transverse dimension that is smaller than the first transverse dimension, and a longitudinal axis extending through the first portion and the second portion, the body further including a projection extending laterally outward relative to the longitudinal axis;
    where the channel is configured to removably receive a portion of the intraosseous device having a hub and a cannula extending from the hub, with the first portion of the channel receiving a part of the hub and configured to prevent rotation of the hub, and the second portion of the channel receiving a part of the cannula while preventing passage of the hub through the second portion;
    where the body includes a protrusion defined by a bump formed on an inner surface of the body and extending from the inner surface of the body into the first portion of the channel, the protrusion fixed relative to the first portion of the channel and configured to extend into a recess in the hub of the intraosseous device when the intraosseous device is received in the channel to resist movement of the intraosseous device away from the second portion of the channel; and where a lateral portion of the channel is open between the first end of the body and the second end of the body, and where the lateral portion of the channel is configured to prevent laterally inserting the hub into the channel, such that the portion of the intraosseous device can be disposed in the channel by laterally inserting the cannula into the channel with the hub outside of the channel and then longitudinally advancing the hub in a direction toward the body such that the hub is received in the channel.

8. The apparatus of claim 7, where the body further includes a second projection extending outwardly relative to the longitudinal axis.

9. The apparatus of claim 7, where the first portion of the channel has a non-circular cross-sectional shape configured to prevent the rotation of the hub of the intraosseous device relative to the body when the portion of the intraosseous device is disposed in the channel.

10. The apparatus of claim 9, where the first portion of the channel is defined by a plurality of planar surfaces configured to prevent the rotation of the hub of the intraosseous device relative to the body when the part of the hub is disposed in the first portion of the channel.

11. The apparatus of claim 7, where the protrusion is integrally formed with the body.

12. A method comprising:
disposing a portion of an intraosseous device in a channel of an assistive device configured to removably receive the portion of the intraosseous device, the intraosseous device comprising a hub having an opening and a cannula extending from the hub to a distal end, the assistive device comprising a body defining the channel having a longitudinal axis and receiving a portion of the cannula and preventing passage of the hub through the channel, the channel further receiving the portion of the intraosseous device with a first portion of the channel receiving a part of the hub and preventing rotation of the hub, and the body further including at least one projection extending laterally outward relative to the longitudinal axis of the channel, and the channel configured to laterally receive the intraosseous device by laterally inserting the cannula into the channel with the hub outside of the channel such that laterally inserting the hub into the channel is prevented, and then longitudinally advancing the hub in a direction toward the body such that the hub is received in the channel, where the hub includes a recess, and the body of the assistive device includes a protrusion defined by a bump formed on an inner surface of the body and extending from the inner surface of the body into the first portion of the channel in the assistive device, the bump fixed relative to the first portion of the channel and configured to extend into the recess of the hub to resist movement of the hub away from the channel;

inserting an elongated member of an ejector into a lumen of the cannula through the opening in the hub, the ejector further comprising a head at one end of the elongated member; and pushing the head and assistive device together to cause a distal end of the elongated member to push a biological sample through the distal end of the cannula.

13. The method of claim 12, where the body of the assistive device includes a first end and a second end, and defines the channel with the first portion having a first transverse dimension, a second portion disposed between the first portion and the second end and having a second transverse dimension that is smaller than the first transverse dimension, the longitudinal axis extends through the first portion and the second portion, and the second portion receiving a part of the cannula while preventing passage of the hub through the second portion.

14. The method of claim 13, where the hub of the intraosseous device has a non-circular perimeter and the first portion of the channel in the assistive device is shaped to prevent the rotation of the hub relative to the assistive device.

15. The method of claim 14, where the first portion of the channel is defined by a plurality of planar surfaces configured to prevent the rotation of the hub relative the assistive device.

16. The method of claim 13, where a lateral portion of the channel in the body of the assistive device is open between the first end and the second end of the body, and where disposing the portion of the intraosseous device in the channel of the assistive device further comprises laterally inserting the intraosseous device into the channel.

17. The method of claim 12, where each projection of the assistive device defines a gripping surface facing away from a first end of the body of the assistive device.

18. The method of claim 12, where the protrusion is integrally formed with the body of the assistive device.

\* \* \* \* \*